United States Patent
Poulsen et al.

(10) Patent No.: US 10,117,608 B2
(45) Date of Patent: Nov. 6, 2018

(54) MOUNTING DEVICE FOR AN ELECTROCHEMICAL SENSOR UNIT

(75) Inventors: Ebbe Helt Poulsen, Højagervej (DK); Henrik Olsson, Frem (DK)

(73) Assignee: Radiometer Medical APS, Bronshoj (DK)

( * ) Notice: Subject to any disclaimer, the term of this patent is extended or adjusted under 35 U.S.C. 154(b) by 1157 days.

(21) Appl. No.: 11/730,195

(22) Filed: Mar. 29, 2007

(65) Prior Publication Data

US 2007/0238943 A1 Oct. 11, 2007

(30) Foreign Application Priority Data

Apr. 7, 2006 (DK) ................................ 2006 00506

(51) Int. Cl.
*A61B 5/00* (2006.01)
*A61B 5/145* (2006.01)
*A61B 5/1477* (2006.01)

(52) U.S. Cl.
CPC ........ *A61B 5/14542* (2013.01); *A61B 5/1477* (2013.01); *A61B 5/6833* (2013.01)

(58) Field of Classification Search
CPC .................................................. A61B 5/14532
USPC .......................... 600/345; 128/632, 635, 640
See application file for complete search history.

(56) References Cited

U.S. PATENT DOCUMENTS

| 4,274,418 | A  | * | 6/1981  | Vesterager et al. | ........... 600/354 |
| 4,809,698 | A  | * | 3/1989  | Kogo             | ............ 600/364 |
| 6,878,262 | B2 | * | 4/2005  | Taniike et al.   | ............ 205/777.5 |
| 2004/0147885 | A1 | * | 7/2004  | Tsuda et al.  | ................. 604/313 |
| 2006/0271015 | A1 | * | 11/2006 | Mantell       | ........................ 604/533 |

FOREIGN PATENT DOCUMENTS

| JP | 60-064391      | 5/1985 |
| WO | WO 2006/017358 A | 2/2006 |

* cited by examiner

*Primary Examiner* — Christian Jang
(74) *Attorney, Agent, or Firm* — Finnegan, Henderson, Farabow, Garrett & Dunner, LLP

(57) ABSTRACT

A device for mounting an electrochemical sensor unit to a skin surface of a human being comprises a mounting member having a circumferential wall, an adhesive tape at a lower end of the circumferential wall for adhering the mounting member to the skin surface, and a sealing member. The sealing member provides a liquid tight seal between a lumen or measuring chamber defined between the skin surface, the mounting device and the sensor unit, the measuring chamber being normally filled with a contact liquid. Alternatively, the sealing member is provided on the sensor unit. The provision of the sealing member renders the system less vulnerable to force impacts and reduces the risk of flawed measurements due to atmospheric air in the measuring chamber. The electrochemical sensor unit may e.g. be suitable for transcutaneous measurement of partial carbon dioxide pressure ($pCO_2$) or partial oxygen pressure ($pO_2$).

13 Claims, 4 Drawing Sheets

MOUNTING DEVICE FOR AN ELECTROCHEMICAL SENSOR UNIT

TECHNICAL FIELD

The present invention relates to a device for mounting of an electrochemical sensor unit to a skin surface of a human being. The sensor unit may in particular be suitable for transcutaneous measurement of gas, especially oxygen and carbon dioxide, diffusing from the blood vessels and through skin tissue. On the basis of such a transcutaneous measurement of, e.g. oxygen, it is possible to estimate the arterial partial pressure of oxygen in surveying the condition of a patient, such as a neonate or a patient under anaesthesia. Transcutaneous measurements may also be useful in wound diagnostics or wound care, e.g. to determine the presence of necrotic tissue.

BACKGROUND OF THE INVENTION

Sensors of the above-mentioned type may be mounted to the patient's skin surface by means of a mounting device, which in turn is adhered to the skin surface. The mounting device may comprise a ring-shaped member that extends upwardly from the skin surface and includes a fastener for securing the sensor thereto. When the sensor is secured to the mounting device, a measuring chamber is defined by an inner surface of the mounting device, the skin surface, and a lower surface of the sensor. Following application of the mounting device to the skin surface, but prior to mounting of the sensor in the mounting device, drops of contact gel or liquid may be applied to the skin surface so that the liquid essentially fills the measuring chamber once the sensor has been mounted to the mounting device. As gases, such as oxygen and/or carbon dioxide, diffuse through the skin surface, the partial pressures of these gases in the measuring chamber become representative of the arterial and/or dermatologic partial gas pressures.

Recent development activities have aimed at reducing the dimensions of the sensor and the mounting device. However, as dimensions reduce, the sensors become more vulnerable to mechanical impact due to, e.g., movements of parts of patients' bodies. In particular, tests have shown that atmospheric air entering the measuring chamber may influence the partial gas pressures of e.g. oxygen and carbon dioxide in the measuring chamber to such an extent that measurements become non-representative of the arterial partial gas pressures.

SUMMARY OF THE INVENTION

It is therefore an object of preferred embodiments of the present invention to provide a mounting device for an electrochemical sensor unit that is less vulnerable to mechanical impact. It is a further object of preferred embodiments of the present invention to provide a combination of an electrochemical sensor unit and a mounting device for the electrochemical sensor unit that is less vulnerable to mechanical impact. Further objects of preferred embodiments of the invention are to provide a mounting device and combination that avoid or at least reduce the risk of flawed measurements due to atmospheric air in the measuring chamber.

A first embodiment provides a device for mounting an electrochemical sensor unit to a skin surface of a human being, comprising:

a mounting member comprising a circumferential wall;
an adhesive tape at a lower end of the circumferential wall for adhering a lower end of the mounting member to the skin surface; and
at least one sealing member extending along the circumferential wall.

A second embodiment provides a combination of an electrochemical sensor unit and a device for mounting of the sensor unit to a skin surface of a human being, wherein the device comprises:

a mounting member comprising a circumferential wall, whereby the circumferential wall defines an inner surface facing an interior lumen of the mounting member and an outer surface facing exterior environment;
an adhesive tape for adhering a lower end of the mounting member to the skin surface; the combination further comprising:
at least one sealing member for providing a liquid tight seal between a surface of the sensor unit and the circumferential wall.

It has been found that the provision of the sealing member renders the sensor unit and mounting device less vulnerable to mechanical impact due to e.g. movements of parts of the patient's body, and reduces the risk of entry of atmospheric air into a measuring chamber formed between the circumferential wall, the skin surface and the sensor unit during use thereof, even when the sensor unit and hence the mounting member is subjected to relatively large force impacts. The sealing member preferably seals between the sensor unit and a surface of the circumferential wall, so that it forms a seal of the measuring chamber when the sensor unit is held in firm abutment against the upper surface of the circumferential wall.

In other embodiments, the sealing member may be provided at an upper end of the mounting member, though other arrangements are envisaged, as it will become apparent from the below disclosure.

At its lower end, i.e. at that end which is defined by the skin surface, the measuring chamber is sealed by the adhesive tape, which also serves to adhere the mounting device to the skin surface. The provision of the adhesive tape, which preferably forms a liquid tight seal, may prevent leakage of contact liquid out of the measuring chamber. Additionally the combination of the seal formed by the adhesive tape and the sealing member prevent pressure equalization between the measuring chamber and the exterior environment during use of the mounting device and the associated sensor unit. Consequently, if the sensor unit is pulled away from the skin surface and the volume of the measuring chamber tends to increase, suction is created in the measuring chamber. The suction reduces the risk of unintentional removal of the sensor unit and the mounting device from the skin. The suction also results in the benefit that the adhesive tape may be formed with a smaller surface area than if the suction was not generated, as the adhesive force required to hold the sensor unit in place is reduced.

It will be appreciated that preferred embodiments may comprise three elements: the mounting member, the sealing member, and the adhesive tape. The sealing member may be made from an elastomeric material for achieving the desired sealing properties. The mounting member is preferably made from a more rigid material for achieving mechanical stability. Mechanical stability could also be achieved by forming the mounting member and the sealing member as one integrated part from an elastomeric material. In such a case, the wall thickness of the circumferential wall of the mounting device would be significantly larger than in other preferred embodiments, in which the mounting device is made from a relatively rigid material.

The circumference of the circumferential wall may define any shape fitting the shape of the sensor unit with which the mounting device is intended to be used. The circumference may e.g. define a circular, oval or polygonal shape. In a preferred embodiment, the circumferential wall is cylindrical.

The sealing member preferably comprises a resilient element, such as an elastic circular ring. In a cross-sectional view parallel to a centre axis of the ring, the ring may e.g. have a polygonal, oval or circular cross-section.

An inner portion of the circumferential wall preferably comprises structure for securing the sensor unit to the mounting member and preferably also for holding a surface of the sensor unit in firm abutment against the sealing member of the mounting device. Such structure may e.g. include a threaded portion for engaging a corresponding threaded portion of the sensor unit. An alternative structure may include a snap-fit connection. A further alternative includes a two-side adhesive tape system. Preferably, the interconnection between the sensor unit and the mounting device is releasable, so that the sensor unit may be removed for maintenance or exchange, or application of fresh contact liquid. When the sensor unit is mounted in the mounting device, excess contact gel possibly present in the measuring chamber is expelled and may be dried off.

In one embodiment, the sealing member is provided at, or forms part of, an outer surface of the circumferential wall. An inner surface of the circumferential wall faces an interior lumen of the mounting member, i.e. the measuring chamber. Such an arrangement is particularly beneficial with respect to manufacture of the mounting device, as the sealing member may conveniently be a pulled over the outer surface of the circumferential wall following manufacture thereof by e.g. injection molding. Moreover, injection molding of the mounting device is facilitated, as there is no need for an inwardly facing collar portion or other shape modification of the inner surface of the circumferential wall for providing a support for the sealing member. Additionally, as the sealing member is at the outer surface of the circumferential wall, it everts outwardly when in firm engagement with the sensor unit, which is beneficial with respect to the sealing effect.

In order to reduce the risk of collection of dirt at areas of transition between the sealing member and the circumferential wall, the sealing member may be provided in a portion of reduced wall thickness of the circumferential wall, or in a groove or indentation formed in the circumferential wall. In particular, the wall thickness may be reduced by a dimension essentially equal to a cross-sectional dimension of the sealing member, so that an outer surface of the sealing member lies flush with the outer surface of the circumferential wall. Likewise, if the sealing member is arranged in a groove or indentation, the depth of the groove or indentation may be essentially equal to the cross-sectional dimension of the sealing member. Thereby, cross-sectional transitions of the outer surface of the mounting device in the vicinity of the sealing member may be avoided, and the risk of dirt collection reduced.

The sealing member may form an upper extremity of the mounting member, i.e. it may lie in the plane of or above the plane of an upper surface of the circumferential wall. It may thereby be ensured that a lower surface of the sensor unit abutting the upper surface of the mounting device comes into to contact with the sealing member to confer reliable sealing. In one embodiment, the upper surface of the sealing member defines a plane, which is upwardly offset from an upper surface of the circumferential wall.

Alternatively, the sealing member may be provided on an inwardly surface of the circumferential wall, e.g. in a groove or indentation thereof, which may be provided at any location along the height of the circumferential wall.

In yet alternative embodiments the sealing member forms part of the sensor unit. In such embodiments, the sealing member is preferably provided on a lower surface of the sensor unit, which abuts the upper surface of the mounting device, so that the sealing member is firmly sandwiched between the circumferential wall and the mounting device.

The sensor unit may comprise a central sensor portion projecting downwardly from an enlarged diameter portion of the sensor unit. Hence, the circumferential wall may conveniently be shaped to receive the central sensor portion in the interior lumen, whereby a lower surface of the enlarged diameter portion of the sensor unit preferably abuts an upper surface of the circumferential wall when the sensor unit is mounted in the mounting member. Thus, the lower surface of the enlarged diameter portion may form a sealing surface for the sealing member, which is arranged between the upper surface of the circumferential wall and the lower surface of the enlarged diameter portion of the sensor unit.

An outer circumferential portion of the downwardly projecting central portion of the sensor unit may define outer threads for mating with inner threads formed on an inner surface portion of the circumferential wall to secure the sensor unit relative to the mounting member and to ensure that the sensor unit is held in firm abutment against the upper surface of the circumferential wall of the mounting member and/or against the sealing member.

The sensor unit may be for transcutaneous measurement of any appropriate parameter. For example, the sensor unit may be for the measurement of partial oxygen pressure in the patient's blood ($pO_2$) or partial carbon dioxide pressure in the patient's blood ($pCO_2$).

BRIEF DESCRIPTION OF THE DRAWINGS

Preferred embodiments of the invention will now be further described with reference to the drawings, in which.

DETAILED DESCRIPTION OF THE DRAWINGS

Figure 1:
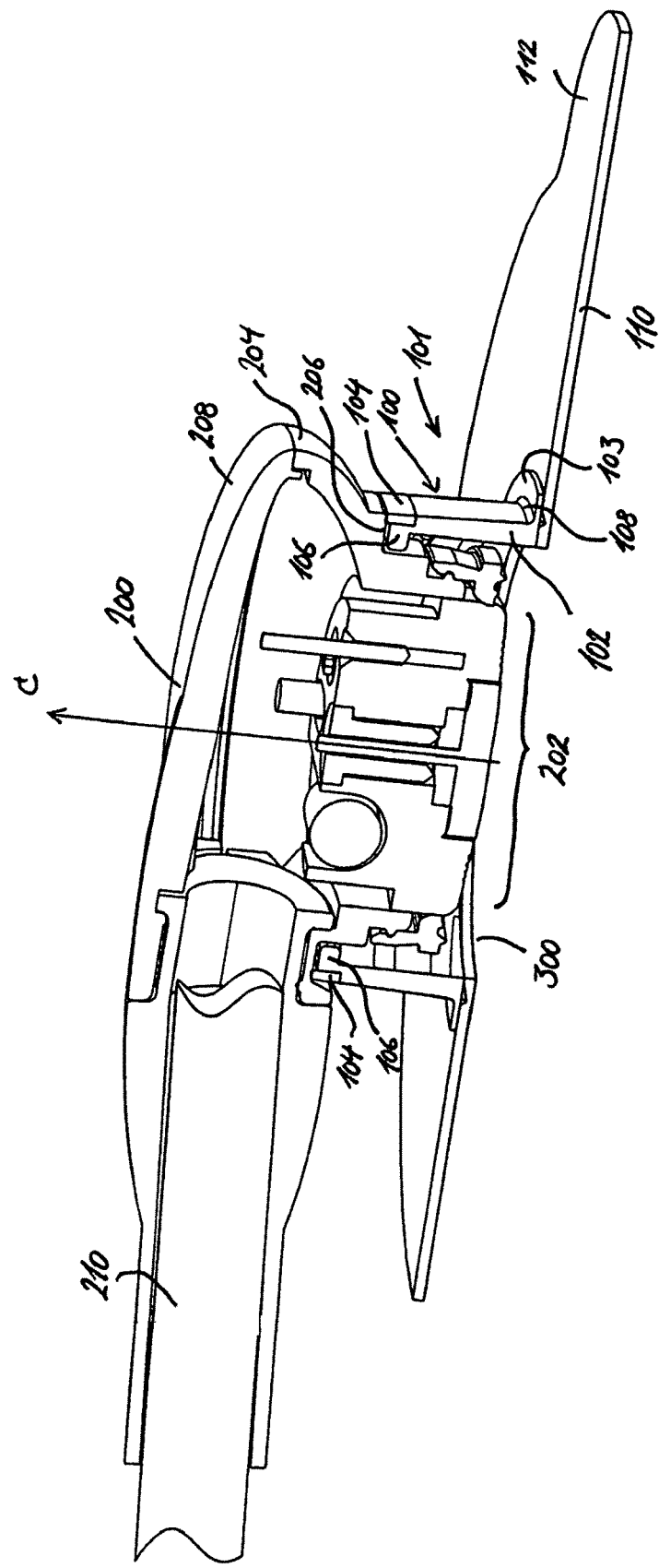
FIG. 1 shows a cross-section of a combination of a sensor unit and a mounting member therefore according to an exemplary embodiment of present invention.

The mounting device 100 shown in FIG. 1 includes a mounting member 101 with a circumferential wall 102 and base 103. The mounting device 100 supports an electrochemical sensor unit 200, comprising internal measuring components 202, a lower cover part 204 defining a downwardly facing surface 206, an upper cover part 208, and an electrical cable 210 for communicating electrical signals produced by the measuring components 202 to a signal processing apparatus (not shown).

At an upper edge of the circumferential wall 102 of the mounting device 100 a sealing member 104 is provided. In the embodiment of FIG. 1, the sealing member 104 comprises an elastomeric sealing ring of rectangular cross section. The sealing member 104 is arranged in an indentation extending circumferentially along the upper edge of the wall 102. The width of the sealing member is essentially equal to the transverse width of the indentation, so that an outer surface of the sealing member 104 is aligned with an outer surface of the circumferential wall 102. An upper extremity of the sealing member 104 extends to a height above an upper extremity of the circumferential wall 102, the upper extremity of the circumferential wall 102, in this example, being defined by an upper surface of an inwardly extending collar portion 106. Thus, it is ensured that the downwardly extending surface 206 of the sensor unit's lower cover part 204 is held in firm abutment with the sealing member 104, when the sensor unit 200 is held in its operating position as shown in FIG. 1, e.g. via mating threads (not shown) in the inner surface of the circumferential wall 102 and in the outer surface of the lower cover part 204, respectively.

The mounting member 101 further forms a lower collar portion 108 supporting an adhesive tape 110 for adhering the mounting member 101 to the skin surface of a human being. In the embodiment of FIG. 1, the adhesive tape 110 is of a generally circular shape with a gripping flap 112 for facilitating handling of the tape during mounting and removal of the mounting device. When the mounting device 100 is mounted to the skin surface and the sensor unit 200 is placed in its operating position in the mounting device 100, an inner lumen or measuring chamber 300 is formed between the skin surface, the outer surfaces of the sensor unit 200 and the inner surfaces of the mounting device 100. In use, the measuring chamber 300 accommodates a contact liquid.

Figure 2:
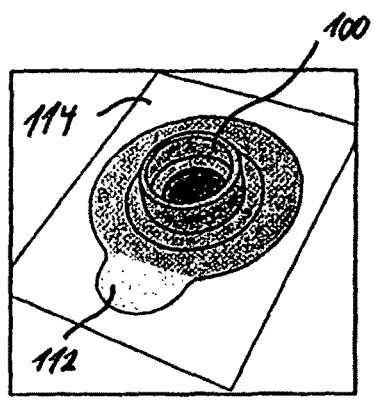
FIGS. 2-6 include a step-by-step illustration of an example of the affixing of a mounting device and a sensor unit to the skin surface of a human being.
Figure 3:
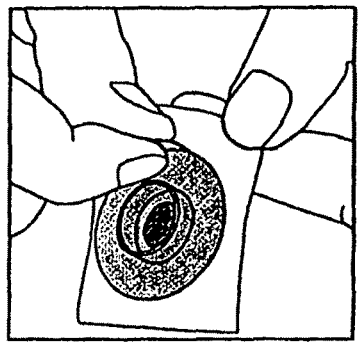
Figure 4:
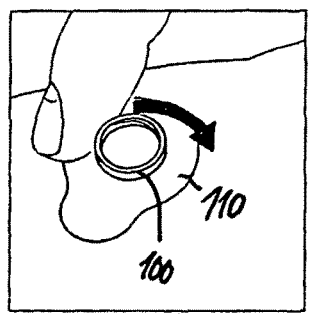
Figure 5:
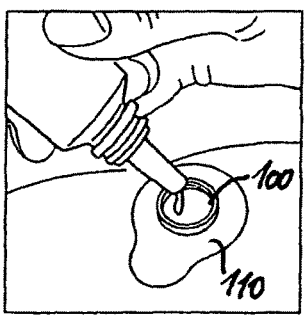
Figure 6:
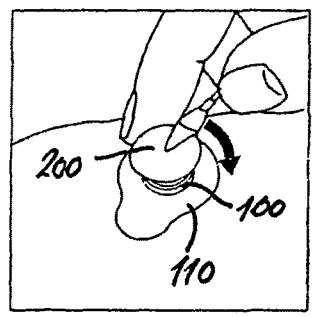

FIGS. 2-6 include a step-by-step illustration of an example of the affixing of the mounting device 100 and the sensor unit 200 to the skin surface of a human being. As shown in FIG. 2, the mounting device 100 is provided as a separate unit with the adhering surface of the adhesive tape 110 covered by a protective film 114. Initially, as shown in FIG. 3, the protective film 114 is peeled off the tape 110, and the mounting device 100 is then placed on the skin surface at an appropriate measuring site, FIG. 4. In order to ensure a tight connection between the adhesive tape 110 and the skin surface, a finger may be run around the upper circumference of the tape 110. Next, a few drops of contact liquid are filled into the inner lumen of the mounting device 100, FIG. 5, and finally the sensor unit 200 is screwed into the mounting device 100, FIG. 6.

Figure 7:
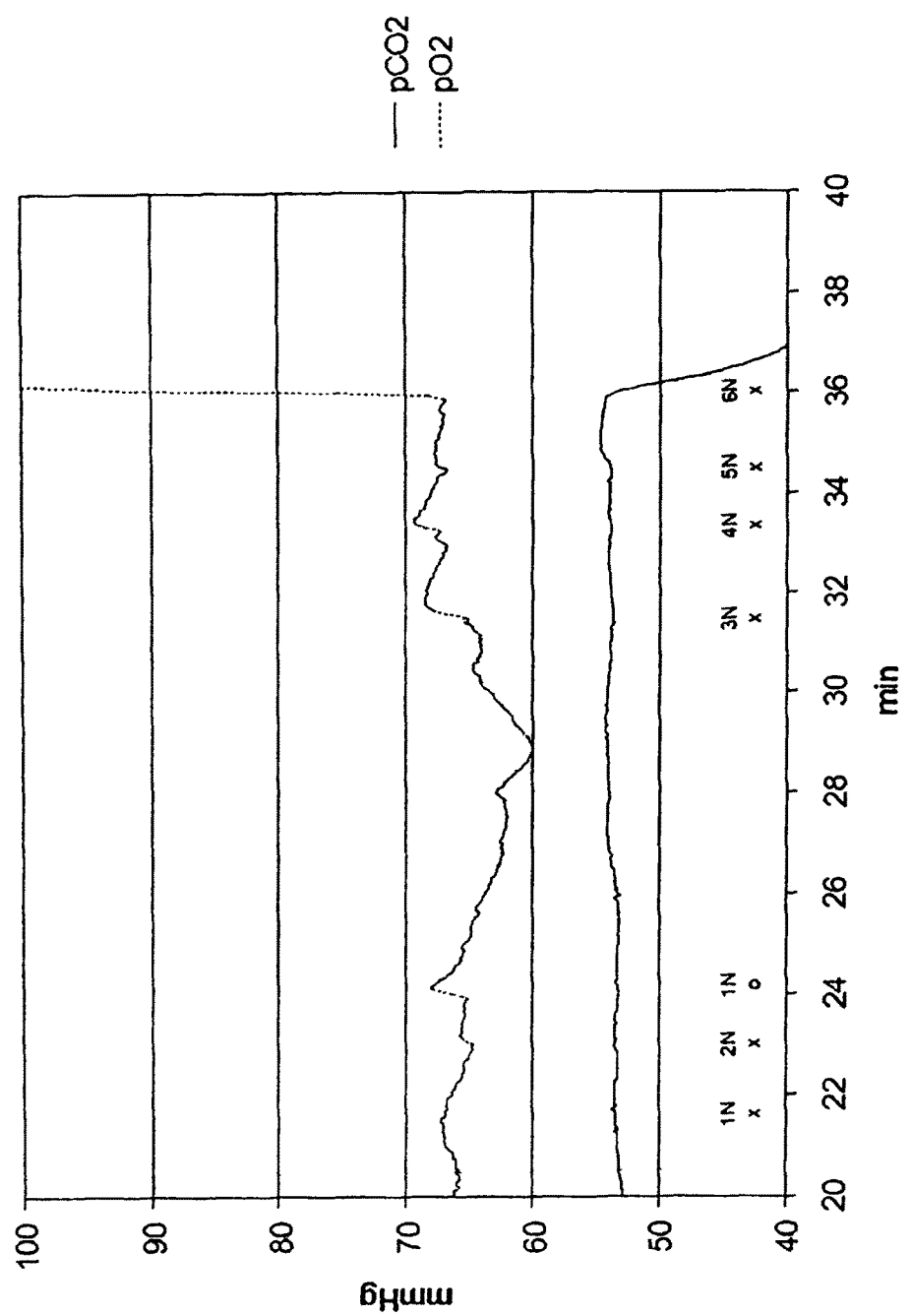
FIG. 7 shows measurements obtained by a combination according to an exemplary embodiment of the present invention.
Figure 8:
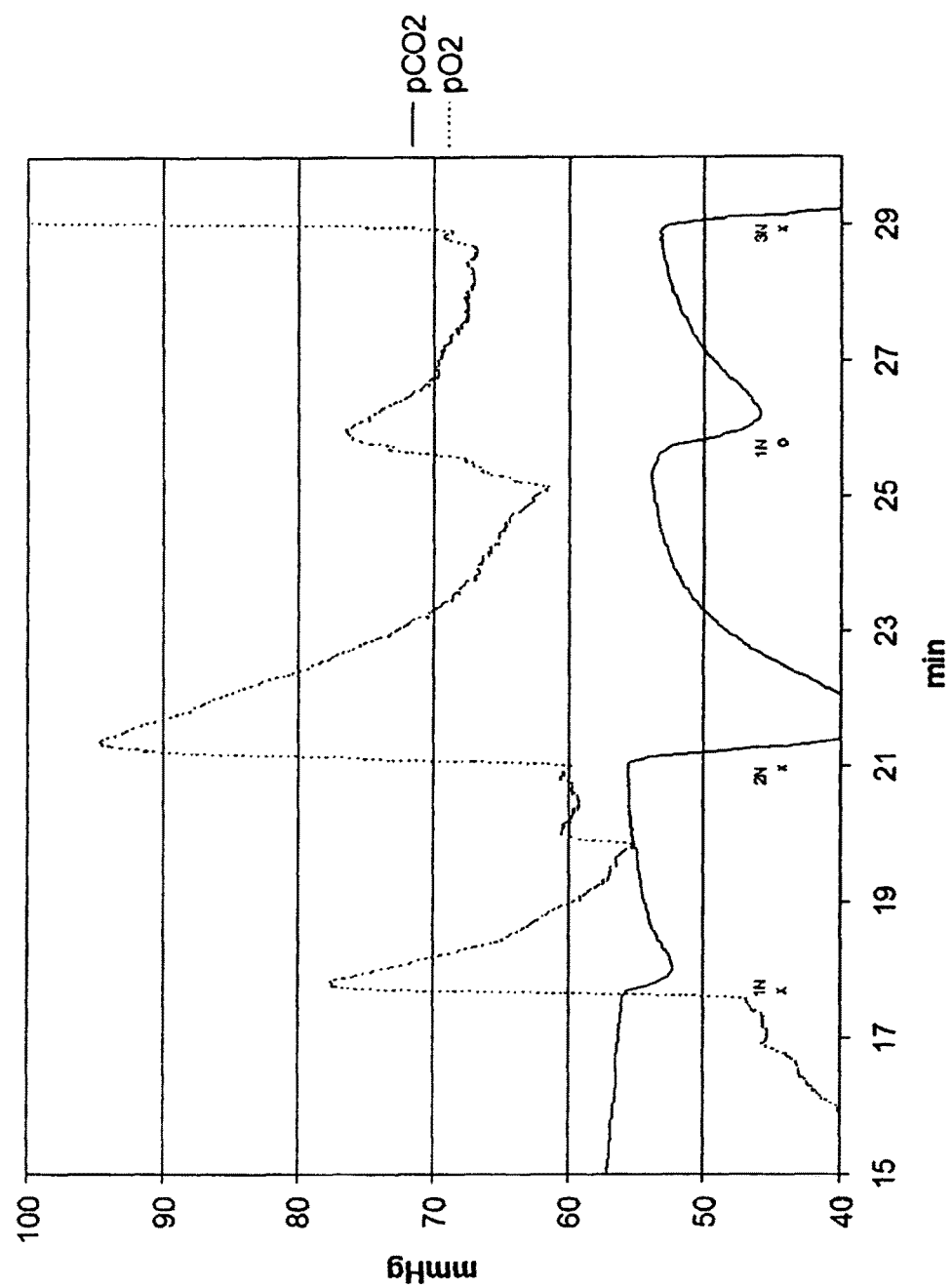
FIG. 8 shows measurements obtained by a combination of a sensor and a mounting device, wherein the combination comprises no sealing member.

The effects of the sealing member 104 become apparent from the measurements shown in FIGS. 7 and 8. It will be noted that the measurements shown in FIGS. 7 and 8 started at 15 to 20 minutes after application of the sensor unit in order to allow the measurements signals to stabilize. Partial carbon dioxide pressure ($pCO_2$) and partial oxygen pressure ($pO_2$) were measured, while different pulls of increasing strength were applied to the sensor unit 200. The pulls were applied in a direction perpendicularly away from the skin surface of a patient (i.e. in the direction of the arrow c in FIG. 1) and parallel to the skin surface of a patient (i.e. perpendicularly to the direction of the arrow c in FIG. 1), respectively. In FIGS. 7 and 8, the occurrence of a pull perpendicular away from the skin surface is indicated by a cross, while the occurrence of a pull parallel to the skin surface is indicated by circle. As shown in FIG. 7, the following forces were applied to the sensor unit:

| Time | Force | Direction | Observation |
| --- | --- | --- | --- |
| 21 min 40 sec. | 1 N | Perpendicular | No significant artifact |
| 23 min. | 2 N | Perpendicular | No significant artifact |
| 24 min 10 sec. | 1 N | Parallel | No significant artifact |
| 31 min 30 sec. | 3 N | Perpendicular | No significant artifact |
| 33 min 20 sec. | 4 N | Perpendicular | No significant artifact |
| 34 min 30 sec. | 5 N | Perpendicular | No significant artifact |
| 36 min. | 6 N | Perpendicular | Significant artifacts |

FIG. 8 shows measurement curves obtained with a system of a sensor unit and a mounting device therefore, including no sealing member. As shown, a pull of 1 N only resulted in significant artifacts.

From the measurements shown in FIGS. 7 and 8 it will thus be appreciated that the provision of the sealing member 104 results in a more stable sensor system, which is less vulnerable to force impacts than systems with no sealing member.

The invention claimed is:

1. A device for mounting an electrochemical sensor unit to a skin surface of a human being, comprising:
   a mounting member, which is a separate element from the electrochemical sensor unit, and comprises a circumferential wall having an inner surface and an outer surface;
   at least one sealing member having an outer surface,
      wherein the sealing member is a separate element from the mounting member and the electrochemical sensor unit and forms an upper extremity of the mounting member,
      wherein the mounting member is made from a more rigid material than the sealing member;
      wherein the sealing member is arranged in an indentation in the outer surface of the circumferential wall without modification to the shape of the inner surface of the circumferential wall to support the sealing member, wherein the indentation is equal to the cross-sectional dimension of the sealing member,
      wherein the outer surface of the sealing member is exposed to the environment exterior to the mounting member,
      wherein the outer surface of the sealing member is aligned with the outer surface of the circumferential wall, and
      wherein the sealing member extends circumferentially along the circumferential wall to provide a seal between a surface of the electrochemical sensor unit and the circumferential wall of the mounting member when the electrochemical sensor unit is mounted to the mounting member, and
   an adhesive member at a lower end of the circumferential wall for adhering a lower end of the mounting member to the skin surface.

2. A device according to claim 1, wherein the at least one sealing member is provided at an upper end of the mounting member.

3. A device according to claim 2, wherein an inner portion of the circumferential wall comprises structure for securing the electrochemical sensor unit to the mounting member.

4. A device according to claim 1, wherein an inner portion of the circumferential wall comprises structure for securing the electrochemical sensor unit to the mounting member.

5. A device according to claim 4, wherein said structure comprises a threaded portion.

6. A device according to claim 1, wherein the sealing member is provided in a portion of reduced wall thickness of the circumferential wall.

7. A device according to claim 1, wherein the mounting member, the sealing member, and the adhesive tape are formed as three separate elements.

8. A combination comprising:
an electrochemical sensor unit;
a device for mounting the electrochemical sensor unit to a skin surface of a human being, said device including:
a mounting member, which is a separate element from the electrochemical sensor unit, and comprises a circumferential wall having an inner surface and an outer surface;
at least one sealing member having an outer surface,
wherein the sealing member is a separate element from the mounting member and the electrochemical sensor unit and forms an upper extremity of the mounting member,
wherein the mounting member is made from a more rigid material than the sealing member;
wherein the sealing member is arranged in an indentation in the outer surface of the circumferential wall without modification to the shape of the inner surface of the circumferential wall to support the sealing member, wherein the indentation is equal to the cross-sectional dimension of the sealing member,
wherein the outer surface of the sealing member is exposed to the environment exterior to the mounting member,
wherein the outer surface of the sealing member is aligned with the outer surface of the circumferential wall, and
wherein the sealing member extends circumferentially along the circumferential wall to provide a seal between a surface of the electrochemical sensor unit and the circumferential wall of the mounting member when the electrochemical sensor unit is mounted to the mounting member, and
an adhesive member at a lower end of the circumferential wall for adhering a lower end of the mounting member to the skin surface.

9. A combination according to claim 8, wherein the electrochemical sensor unit comprises a central sensor portion projecting downwardly from an enlarged diameter portion of the sensor unit, and wherein the circumferential wall is shaped to receive the central sensor portion in said interior lumen, and wherein the enlarged diameter portion defines a lower surface, which abuts an upper surface of the circumferential wall when the electrochemical sensor unit is mounted in the mounting member.

10. A combination according to claim 9, wherein the sealing member is provided at the abutment between the upper surface of the circumferential wall and the lower surface of the enlarged diameter portion of the electrochemical sensor unit.

11. A combination according to claim 9, wherein an outer circumferential portion of the downwardly projecting central portion of the electrochemical sensor unit defines outer threads for mating with inner threads formed on the inner surface of the circumferential wall of the mounting member.

12. A combination according to claim 8, wherein the mounting member, the sealing member, and the adhesive tape are formed as three separate elements.

13. A combination according to claim 8, wherein the electrochemical sensor unit is for transcutaneous measurement of at least one of: partial carbon dioxide pressure ($pCO_2$) and partial oxygen pressure.

* * * * *

UNITED STATES PATENT AND TRADEMARK OFFICE
CERTIFICATE OF CORRECTION

| | | |
|---|---|---|
| PATENT NO. | : 10,117,608 B2 | Page 1 of 1 |
| APPLICATION NO. | : 11/730195 | |
| DATED | : November 6, 2018 | |
| INVENTOR(S) | : Ebbe Helt Poulsen | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1345 days.

Signed and Sealed this
Eighteenth Day of June, 2019

Andrei Iancu
*Director of the United States Patent and Trademark Office*